United States Patent [19]

Pinto

[11] Patent Number: 5,252,609
[45] Date of Patent: Oct. 12, 1993

[54] SYNTHESIS GAS PRODUCTION
[75] Inventor: Alwyn Pinto, Cleveland, England
[73] Assignee: Imperial Chemical Industries PLC, London, England
[21] Appl. No.: 906,307
[22] Filed: Jun. 30, 1992

[30] Foreign Application Priority Data

| Jul. 9, 1991 | [GB] | United Kingdom | 9114838 |
| Sep. 9, 1991 | [GB] | United Kingdom | 9119212 |
| Oct. 11, 1991 | [GB] | United Kingdom | 9121671 |
| Oct. 30, 1991 | [GB] | United Kingdom | 9122987 |

[51] Int. Cl.$^5$ .................. C07C 27/06; C01B 33/02; C01B 3/36
[52] U.S. Cl. .................. 518/703; 518/704; 252/373; 423/359
[58] Field of Search .................. 518/703, 704; 252/373

[56] References Cited

U.S. PATENT DOCUMENTS 4,782,096 11/1988 Banquy .

FOREIGN PATENT DOCUMENTS 212758 3/1987 European Pat. Off. .
3345088 6/1985 Fed. Rep. of Germany .

OTHER PUBLICATIONS

Van Den Berg, P. J. and De Jong, W. A.; "Ch. IV-Production of Ammonia From Natural Gas," Introduction to Chemical Process Technology, (1980: Delft University Press, Delft Holland); pp. 28–51.
European Search Report, EP 92 30 5784, Van Der Poel W., The Hauge, Dec. 3, 1992.

Primary Examiner—Howard T. Mars
Attorney, Agent, or Firm—Cushman, Darby & Cushman

[57] ABSTRACT

Synthesis gas production comprising primary catalytic steam reforming a first stream of desulphurised hydrocarbon feedstock, optionally followed by secondary reforming using an oxygen-containing gas, and then cooling; adiabatically low temperature steam reforming a second stream of the feedstock, preferably adding a hydrogen-containing gas, and then subjecting the product to partial oxidation with an oxygen-containing gas, and then cooling; and mixing the cooled products.

For methanol production, the partial oxidation step pressure may be greater than the primary reforming pressure, and the hydrogen-containing gas is taken from the methanol synthesis loop: if the partial oxidation step is non-catalytic and in the absence of steam, the pre-reforming stage can be omitted. Methanol can be synthesised from the reformed first and/or second streams in an auxiliary synthesis stage at an intermediate pressure before the relevant stream is added to the synthesis loop.

10 Claims, 4 Drawing Sheets

SYNTHESIS GAS PRODUCTION

BACKGROUND TO THE INVENTION

This invention relates to the production of synthesis gas for use for the synthesis of hydrogen-containing compounds such as ammonia or alcohols, e.g. methanol, and to the synthesis of such hydrogen-containing compounds from the synthesis gas.

Such hydrogen-containing compounds are usually synthesised in a synthesis loop wherein a mixture of fresh synthesis gas, termed make-up gas, and recycle gas, is fed at elevated temperature and pressure to a synthesis reactor containing a suitable catalyst for the synthesis reaction. The desired hydrogen-containing compound is then separated from the reacted gas leaving the synthesis reactor, for example by cooling the reacted synthesis gas to condense the synthesised hydrogen-containing compound as a liquid phase which can readily be separated. The gas remaining after separation of the desired hydrogen-containing compound is then recycled to the synthesis reactor as the recycle gas. Since the make-up gas often contains components that are inert in the synthesis reaction and/or an excess of one of the reactants, part of the gas is taken from the loop as a purge to avoid a build-up of inerts, or the reactant that is in an excess, in the gas circulating round the synthesis loop. Often some or all of the purge is subjected to a purification process to recover desired reactants which are recycled, directly to the synthesis as part of the recycle gas, or to a suitable point in the production of the make-up gas. Where the process used to produce the make-up gas includes a separation step effective to remove undesired components, e.g. the excess of one reactant or inerts, the purge can be recycled to a point in the production of the make-up gas upstream of that separation step.

The make-up gas is often produced by a series of steps including steam reforming of a hydrocarbon feedstock, particularly natural gas or naphtha. In this steam reforming stage the feedstock, usually after desulphurisation, is reacted at elevated temperature and pressure with steam, and sometimes also carbon dioxide, over a steam reforming catalyst, commonly nickel supported on a refractory material such as alumina or calcium aluminate, to give a gas stream containing hydrogen, carbon oxides and methane. The reforming catalyst is normally disposed in tubes heated in a furnace fired by a suitable fuel. Some or all of the aforesaid purge gas may be used as at least part of the furnace fuel.

Often, particularly where the process is used to produce ammonia synthesis gas, the primary reformed gas is subjected to a partial oxidation step, often called secondary reforming, wherein the primary reformed gas is partially oxidised with a gas containing free oxygen, e.g. oxygen itself, or air (or oxygen-enriched or oxygen-depleted air) where it is desired to introduce nitrogen into the make-up gas, for example for ammonia synthesis gas. In this secondary reforming step, the partially oxidised, i.e. partially combusted, gas usually is then passed through a steam reforming catalyst to effect further reforming to decrease the methane content. Such a step of partial oxidation followed by passage through a steam reforming catalyst is often termed autothermal reforming. The heat required for the endothermic reforming reaction is thus provided by the heat evolved in the partial combustion. Depending on the intended use, the resultant product gas, i.e. primary reformed gas, or secondary reformed gas where such a partial oxidation step is used, is further treated to give the make-up gas. The further treatment will depend on the intended use.

For ammonia synthesis, the make-up gas is required to contain hydrogen and nitrogen. The secondary reformed gas obtained using air (or oxygen-enriched or oxygen-depleted air) as the oxygen-containing gas will contain hydrogen, nitrogen, carbon oxides, methane and argon. Thus for ammonia synthesis gas the secondary reformed gas is usually subjected to one or more steps of the shift reaction with steam to convert carbon monoxide to carbon dioxide with the production of more hydrogen, and then carbon dioxide and water vapour are removed. Since carbon oxides act as poisons for ammonia synthesis catalysts, the residual carbon oxides are usually removed, for example by methanation. Alternatively, the shifted gas may be subjected to a catalytic selective oxidation to convert the residual carbon monoxide to carbon dioxide and then the carbon dioxide and water vapour removed. Since hydrogen and nitrogen react in the proportions of 3 moles of hydrogen to each mole of nitrogen to produce ammonia, the make-up gas desirably has a hydrogen/nitrogen molar ratio of about 3. While this can be achieved by choosing the primary and secondary reforming conditions so that the amount of air employed is that which introduces the desired amount of nitrogen, in order to reduce the amount of reforming that has to be effected in the primary reformer, the amount of air employed in the secondary reforming step is often such that the autothermally reformed gas contains an excess of nitrogen over that required for ammonia synthesis. Consequently in such cases there will usually be a step of nitrogen removal, either on the make-up gas prior to its addition to the synthesis loop, or on a stream taken from the loop: in the latter case, the excess of nitrogen is separated from the stream taken from the loop, leaving a stream enriched in hydrogen. This hydrogen-enriched stream is then returned to the loop. The separation of the excess of nitrogen also often serves to remove some or all of the residual methane and argon (which act as inerts in the ammonia synthesis process). The resultant gas waste gas stream containing the excess of nitrogen and residual methane thus has some fuel value and so is often used as part, or all, of the fuel employed to heat the primary reformer.

For synthesis of oxygen-containing organic compounds such as methanol, the make-up gas contains hydrogen, carbon monoxide and carbon dioxide. The parameter "R", given by the equation $$R = ([H_2] - [CO_2])/([CO] + [CO_2])$$

where $[H_2]$, $[CO]$, and $[CO_2]$ represent the molar proportions of hydrogen, carbon monoxide and carbon dioxide respectively, is often used in relation to the composition of the make-up gas. A make up gas having a value of "R" equal to 2 has the stoichiometric composition for methanol synthesis.

While a secondary reforming step is often not employed in the manufacture of methanol synthesis gas, its use may enable the synthesis gas to have a composition more suited to methanol synthesis. Thus, in the absence of a secondary reforming step, assuming the feedstock is natural gas, the synthesis gas will contain more hydrogen than is required to convert the carbon oxides present to methanol, i.e. "R" will be well above 2. The use of a secondary reforming step enables the value of "R" to be decreased to a suitable level, e.g. in the range 1.8 to 2.2. Thus it has been proposed in GB-A-2099846 to operate the primary reforming stage at pressures in the range 35 to 55 bar abs., using lower outlet temperatures than is conventional, to give a gas stream containing a relatively high methane content and then to subject this primary reformed gas to secondary reforming with oxygen.

For synthesis gas to be used for the manufacture of oxygenated organic compounds such as methanol, the reformed gas, after secondary reforming (if such a step is employed), may need no further treatment except cooling and removal of water vapour.

The aforesaid primary reforming step employing catalyst-containing tubes heated in a fired furnace is not very efficient thermally and involves large and costly installations. There have been various proposals for decreasing the duty of primary reformers, e.g. by partially bypassing the primary reformer so that part of the feed is fed directly to the secondary reformer. Thus in order to increase the throughput of existing plants, it has been proposed in e.g. GB-A-2160516 to provide a partial bypass of the primary reformer so that some of the feedstock is fed directly to the secondary reformer. A similar process is described in GB-A-1569014. Also the bypassing of the primary reformer means that the overall steam ratio can be decreased so that the volume of gas that has to be cooled, per volume of carbon oxides produced, is less.

These processes however present some difficulties as it is necessary to mix the relatively cold feedstock bypassing the primary reformer with the hot primary reformed gas, and/or to design the secondary reformer with the provision of a separate, additional, feed thereto. The provision of such a separate additional feed presents mixing problems while the addition of the bypass feedstock to the hot primary reformed gas presents problems particularly where it may be desirable to isolate the bypass stream while maintaining the primary and secondary reforming stages in operation.

This isolation ability is particularly desirable where, as suggested in the aforementioned GB-A-2160516 the feedstock is liquid at room temperature, e.g. naphtha, and the feedstock bypassing the primary reformer is subjected to an adiabatic catalytic reaction with steam to produce a gas containing methane as essentially the major hydrocarbon component. Such an adiabatic process, which is herein termed a pre-reforming process, is desirable in order to avoid the carbon deposition which is liable to occur through thermal cracking of hydrocarbons of higher molecular weight than methane when the bypass gas is mixed with the hot product from the primary reformer. Unfortunately the life of the catalyst employed in such an adiabatic pre-reforming process is generally far less than that of the primary or secondary reforming catalysts and so the pre-reforming catalyst will require changing far more frequently than the primary or secondary reforming catalyst. It is therefore desirable to provide for the pre-reforming catalyst to be changed without shutting down the primary and secondary reformers, and so in the aforementioned arrangement wherein the bypass gas, after the pre-reforming stage, is mixed with the hot primary reformed gas, or is fed directly to the secondary reformer, some valve means capable of operating at high temperatures is necessary to effect that isolation.

BRIEF DESCRIPTION OF THE INVENTION

In the present invention the above problems are avoided by employing a separate partial oxidation step to which the bypass feedstock is fed after a pre-reforming stage. The product from this separate partial oxidation stage is cooled and then added to the cooled main process stream after any secondary reforming stage treating the product from the primary reformer. In this way isolation of the bypass stream can be effected with valves operating at relatively low temperatures, below about 600° C.

Accordingly the present invention provides a process for the production of a hydrogen-containing synthesis gas from a desulphurised hydrocarbon feedstock comprising a) subjecting a first stream of said desulphurised feedstock to primary catalytic steam reforming, optionally followed by secondary reforming of the primary reformed gas using an oxygen-containing gas, and then cooling of the resultant reformed first stream; b) subjecting a second stream of said desulphurised feedstock to a pre-reforming step of adiabatic low temperature steam reforming, followed by partial oxidation of the resultant pre-reformed second stream using an oxygen-containing gas, to form a reformed second stream, cooling the reformed second stream; and c) mixing the cooled reformed first and second streams.

In a preferred form of the invention a hydrogen-containing gas, preferably taken from the synthesis loop to which the synthesis gas is fed, is added to the pre-reformed gas prior to the partial oxidation step.

In a particular form of the invention applicable when methanol is being produced from the synthesis gas, the partial oxidation step is effected at a pressure greater than that employed for the primary reforming step: in a preferred variant of this process, a hydrogen-containing gas stream taken from the methanol synthesis loop is added to the second stream before the partial oxidation stage. In a modification of this variant, the partial oxidation step is effected non-catalytically, possibly in the substantial absence of steam: in this instance the pre-reforming stage can be omitted.

In one form of the invention applicable to the production of methanol, methanol is synthesised from the reformed first or second streams, or from a mixture of the reformed first and second streams, in an auxiliary synthesis stage at an intermediate pressure before the relevant stream is added to the synthesis loop.

GENERAL DESCRIPTION OF THE INVENTION

Suitable hydrocarbon feedstocks include hydrocarbons having a boiling point at atmospheric pressure below about 220° C. such as natural gas or naphtha. When producing methanol synthesis gas by the present invention, it is preferred that the hydrocarbon feedstock has an average hydrogen to carbon atomic ratio above 2, particularly above about 2.4: natural gas is the preferred hydrocarbon feedstock for making methanol synthesis gas.

Prior to use, the hydrocarbon feedstock should be desulphurised: this may be effected by passing the feedstock through a bed of a suitable absorbent, for example zinc oxide, to absorb any hydrogen sulphide present. Where the feedstock contains carbon-containing sulphur compounds, these should be converted to hydrogen sulphide prior to passing the gas through the hydrogen sulphide absorbent by adding a small proportion of hydrogen, e.g. part of the make-up gas or loop purge gas, to the feedstock and passing the mixture through a hydrodesulphurisation catalyst, e.g. nickel or cobalt molybdate.

The first stream may contain about 20-95%, particularly particularly at least 30%, of the total feedstock while the second stream correspondingly contains the balance, i.e. 5-80%, and particularly at least 10%, of the total feedstock. For the production of methanol synthesis gas, the first stream preferably is 30-95%, particularly less than 90%, of the total feedstock.

The primary, and any secondary, reforming of the first stream may be effected under conventional conditions, using conventional steam reforming catalysts, e.g. nickel supported on a refractory support of e.g. alumina or calcium aluminate. The primary reformer feed may typically contain 2 to 6, and preferably 2.5 to 3.5, moles of steam per gram atom of hydrogen carbon in the feedstock. Some of the steam may be replaced by carbon dioxide if a source thereof is available. The pressure may be in the range 5-45 bar abs. with primary reforming outlet temperatures in the range 700° to 870° C. and secondary reforming (if used) outlet temperatures in the range 850°-1100° C. However the primary reforming stage may be effected at higher pressure but using a lower outlet temperature than is conventional practice. For example the primary reforming stage may be operated at a pressure in the range 25-45 bar abs., particularly 30-40 bar abs., with an outlet temperature in the range 750°-850° C., particularly 800°-850° C.

When producing methanol synthesis gas with no step of secondary reforming of the first stream, as a result of the use of higher pressures, lower temperatures, and, possibly, lower steam ratios than is conventional, the methane content of the primary reformed gas will be somewhat greater than is conventional and in particular is preferably at least 5%, and particularly in the range 6-15%, by volume on a dry basis. Although this larger amount of methane is fed to the synthesis loop, as will be described hereinafter, some of this methane can be re-used as feedstock.

If ammonia synthesis gas is being produced using a gas, e.g. air, containing nitrogen as well as oxygen, in a secondary reforming stage to further reform the primary reformed first stream and the secondary reformed gas is subsequently subjected to one or more stages of shift, the amount of oxygen-containing gas used in the secondary reforming of the first stream may be such that the secondary reformed first stream has a hydrogen-equivalent to nitrogen molar ratio in the range from about 2.5 up to 3.2 or even higher, e.g. up to 4.0. [By the term "hydrogen-equivalent" we mean the sum of the molar amounts of hydrogen and carbon monoxide in the secondary reformed gas: since in the subsequent shift stage or stages most of the carbon monoxide is converted to carbon dioxide with the production of a corresponding quantity of hydrogen, any carbon monoxide in the secondary reformed gas can be considered to be equivalent to the same molar amount of hydrogen].

In the process of the invention, the portion of the feedstock that bypasses the primary reforming step, i.e. the second stream, is subjected to the low temperature adiabatic reforming step, i.e. pre-reforming step, irrespective of the nature of the feedstock. This ensures that any hydrocarbons of molecular weight greater than that of methane, e.g. the small amounts of ethane, propane, etc. present in predominantly methane feedstocks such as natural gas, are converted before the bypass stream is subjected to high temperatures.

In the pre-reforming step, i.e. low temperature adiabatic steam reforming process, the second feedstock stream mixed with steam is preheated to a temperature typically in the range 400°-700° C., and passed over a low temperature steam reforming catalyst having steam reforming activity at temperatures below about 650° C., particularly below about 550° C. The pressure at which this stage is operated may be about the same as that employed for the primary reforming of the first stream. Alternatively it may be desirable, particularly where the reformed second stream, i.e. after the partial oxidation step, is not subjected to further chemical reaction steps, e.g. shift, prior to compression, for example in the production of methanol synthesis gas, to operate the processing of the second stream at a significantly higher pressure than that employed in the processing of the first stream, e.g. at pressures in the range up to about 100 bar abs. Further description of this aspect of the invention for the production of methanol synthesis gas is described hereinafter.

The steam to hydrocarbon carbon ratio for the pre-reforming of the second stream is preferably less than that employed in the primary reforming of the first stream: for example the amount of steam in the second stream is typically 0.5 to 2, preferably 1-2, moles per gram atom of hydrocarbon carbon. As a result, it is usually necessary to divide the desulphurised feedstock prior to steam addition or to add further steam to the first stream prior to primary reforming thereof. Alternatively, and especially where the processing of the second stream is effected at a different pressure from that of the first stream, separate desulphurised feedstocks may be used.

Suitable catalysts for the low temperature steam reforming stage are those catalysts employed in the well known CRG process for the production of synthetic natural gas from naphtha feedstocks and may comprise the reduction products of nickel oxide obtained by precipitation. Typical catalysts, before reduction, comprise at least 60% by weight of nickel oxide. The nickel oxide is usually stabilised by the inclusion of an oxide of a difficultly reducible element such as aluminium and/or magnesium. Such oxide mixtures may result from calcination of co-precipitated compounds of nickel and the difficultly reducible element. Examples of such co-precipitated compounds are nickel aluminium hydroxy carbonates, or nickel magnesium aluminium hydroxy carbonates, e.g. $Ni_6Al_2(OH)_{16}CO_3.4H_2O$ and $Ni_5MgAl_2(OH)_{16}CO_3.4H_2O$. Some or all of the nickel may be replaced by cobalt.

The reaction of the feedstock and steam over the low temperature reforming catalyst is effected adiabatically. Thus the feedstock and steam are heated to the desired inlet temperature and passed through a bed of the catalyst. Higher hydrocarbons react with steam to give carbon oxides and hydrogen: at the same time methanation of the carbon oxides with the hydrogen takes place to form methane. The net result is that the higher hydrocarbons are converted to methane with the formation of some hydrogen and carbon oxides. Some endothermic reforming of methane may also take place, but since the equilibrium at such low temperatures lies well in favour of the formation of methane, the amount of such methane reforming is small so that the product from this stage is a methane-rich gas. The heat required for the reforming of higher hydrocarbons is provided by heat from the exothermic methanation of carbon oxides (formed by the steam reforming of methane and higher hydrocarbons) and/or from the sensible heat of the feedstock and steam fed to the catalyst bed. The exit temperature will therefore be determined by the temperature and composition of the feedstock/steam mixture and may be above or below the inlet temperature. The conditions should be selected such that the exit temperature is lower than the limit set by the de-activation of the catalyst. While some catalysts commonly used in the CRG process are deactivated at temperatures above about 550° C., other catalysts that may be employed can tolerate temperatures up to about 700° C.

While the invention is of utility where the feedstock is naphtha, the present invention may also be employed with natural gas as the feedstock: the amount of hydrocarbons containing two or more carbon atoms in natural gas is generally quite small, less than 10 mole %, and so the amount of exothermic reaction taking place is such that the exit temperature may be below, or not more than about 10° C. above, the inlet temperature.

In order that the amount of oxygen-containing gas required in the second stream partial oxidation stage can be kept at an economic level, e.g. so that where air is employed the amount of nitrogen is in not too great an excess for ammonia synthesis or so that the "R" value is in the desired range for synthesis gas for the production of oxygen-containing organic compounds, it is desirable to heat the feed to the second stream partial oxidation stage to a high temperature, desirably above 500° C., e.g. 620°-800° C.

To minimise the risk of thermal cracking of the methane in the product from the low temperature adiabatic reforming stage during such heating prior to feeding to the second stream partial oxidation stage, it is preferred to add a hydrogen-containing stream, e.g. taken from the synthesis loop, to that product stream prior to heating thereof: this ensures that there is sufficient hydrogen in the mixture heated to the second stream partial oxidation stage inlet temperature that thermal cracking of methane is inhibited. The presence of hydrogen in the feed to the second stream partial oxidation stage also ensures that the autoignition temperature of the mixture is sufficiently low that combustion readily takes place.

In the treatment of the second stream, after the adiabatic reaction over the low temperature reforming catalyst, a hydrogen-containing stream is therefore preferably added and the resultant mixture is heated, for example in a fired heater, to the desired second stream partial oxidation stage inlet temperature. In some cases it may be desirable to subject the methane-rich gas from the low temperature adiabatic reforming step to one or more stages of adiabatic reforming at higher temperatures than that employed in the initial adiabatic reforming stage, prior to any addition of a hydrogen-containing stream and heating to the desired inlet temperature of the second stream partial oxidation stage. For example as described in U.S. Pat. No. 3795485 or U.S. Pat. No. 4383982, the gas may be heated in a fired heater then passed through a bed of a steam reforming catalyst, wherein reforming takes place adiabatically. There may be more than one such adiabatic reforming stage with heating of the gas stream between each adiabatic reforming stage. Since the low temperature adiabatic reforming stage is generally effected using low steam to hydrocarbon carbon ratios, it may be necessary to add a further quantity of steam prior to the autothermal reforming stage. Where one or more such adiabatic reforming stages are employed to effect steam reforming of the methane-rich gas prior to the autothermal reforming step, steam may be added prior to such an adiabatic reforming step. The advantage of employing such an adiabatic reforming stage is that the amount of oxygen-containing gas used in the second stream autothermal reforming stage can be decreased.

As indicated above, after the low temperature adiabatic reforming stage, and after any higher temperature adiabatic reforming stages, a hydrogen-containing gas, preferably taken from the synthesis loop, is preferably added and the mixture heated to the desired inlet temperature of the second stream partial oxidation stage. To minimise the amount of oxygen-containing gas employed in the second stream partial oxidation stage, this oxygen-containing gas is preferably heated as much as is practical. However where the oxygen-containing gas is oxygen, e.g. as produced by an air separation plant, metallurgical considerations limit the amount of preheating of the oxygen-containing gas to about 250° C. However where air is employed as the oxygen-containing gas, the air can conveniently be preheated to a temperature above 650° C., typically in the range 700°-850° C. The feed and oxygen-containing gas preheating temperatures, relative proportions thereof, and amount of any added hydrogen-containing gas should be such that the mixture of the feed (including any added hydrogen-containing gas) and oxygen-containing gas has a temperature above the autoignition temperature of that mixture. Preferably the amount of hydrogen-containing gas added is such that the feed to the second stream partial oxidation stage has a hydrogen content of at least 9% by volume. The amount of hydrogen in the feed to the partial oxidation stage, i.e. before addition of the oxygen-containing gas, is preferably at least 2.5 times the volume of oxygen added in the partial oxidation stage. The second stream partial oxidation step is preferably operated at a steam to hydrocarbon carbon ratio in the range 1 to 2.5, particularly 1 to 2, and at an outlet temperature in the range 950°-1400° C., particularly 950°-1250° C. if the partial oxidation is catalytic and 1100°-1400° C. if the partial oxidation is non-catalytic.

In the production of ammonia synthesis gas using a gas, e.g. air, containing nitrogen as well as oxygen, the amount of such oxygen/nitrogen gas employed is preferably such that the hydrogenequivalent to nitrogen molar ratio of the reformed second stream, i.e. after the partial oxidation stage, is in the range 1.0 to 2.0.

The product stream from the second stream partial oxidation stage is then cooled to a temperature, preferably below about 500° C., appropriate for addition to the reformed first stream. This is conveniently effected by quenching with cold water. The cooled reformed second stream is then added to the cooled reformed first stream and the mixture further processed as necessary to produce the make-up gas fed to the synthesis loop. Alternatively the cooling may include steam raising and/or superheating, boiler feed water heating, and/or reactants preheating. As indicated above the further processing will depend on the nature of the desired synthesis: for ammonia, the further processing will normally include one or more stages of the shift reaction, steam and carbon oxides removal, compression to the synthesis loop pressure, and drying, while for methanol synthesis, the further processing will normally include steam removal and compression. Where the further processing includes shift, the reformed first and second streams are preferably cooled to about the shift inlet temperature prior to mixing.

Accordingly in a preferred form of the invention the primary reformed first stream is subjected to secondary reforming with air before cooling the reformed first stream, and the cooled reformed first and second streams are subjected to the shift reaction, carbon oxides removal, and drying before or after mixing. Preferably the cooled reformed first and second streams are fed as make-up gas to an ammonia synthesis loop having a catalytic ammonia synthesis stage and a separation stage with recycle of unreacted gas from the separation stage to the synthesis stage, and ammonia is synthesised in said synthesis stage from the mixture of make-up gas and recycle gas.

Alternatively, where the reformed second stream does not contain synthesis catalyst poisons, e.g. as in the case of synthesis gas for methanol synthesis, the reformed second stream may, after cooling and, optionally water removal, be added directly to the synthesis loop so that mixing of the first and second streams is effected in the loop. Accordingly, in a preferred form of the invention the cooled reformed first and second streams are fed as make-up gas to a methanol synthesis loop having a catalytic methanol synthesis stage and a separation stage with recycle of unreacted gas from the separation stage to the synthesis stage, and methanol is synthesised in said synthesis stage from the mixture of make-up gas and recycle gas.

In the production of ammonia, it is usual, as indicated above, to subject the secondary reformed gas stream, after cooling, to one or more stages of shift conversion, followed by carbon dioxide removal and methanation, prior to addition to the synthesis loop. In the process of the invention it may be desirable to similarly treat the reformed second stream prior to addition thereof to the first stream or to the loop. Thus the reformed second stream may be subjected to one or more stages of shift followed by carbon dioxide removal and then the carbon dioxide-depleted second stream is added to the first stream before, or after, methanation of the latter. The shifting of the second stream is preferably effected in a single stage, for example in a catalyst bed in heat exchange with a cooling medium, with an outlet temperature in the range 230° to 280° C. An example of such a shift process is described in U.S. Pat. No. 4721611.

In this variant of the process, the carbon dioxide removal from the second stream may be effected by pressure swing adsorption. It has been proposed to employ pressure swing adsorption to separate not only carbon dioxide from the shifted second stream, but also to remove the excess of nitrogen. While pressure swing adsorption removing both carbon dioxide and the excess of nitrogen may be adopted in the present variant, so that the carbon dioxide-depleted second stream has a hydrogen to nitrogen molar ratio of the order of 2.7 to 3.0 or more, it may be more economic to design the pressure swing adsorption stage of the treatment of the second stream to remove carbon dioxide but only part of the excess of nitrogen. The remainder of the excess of nitrogen can then be removed by a hydrogen recovery stage treating the purge from the ammonia synthesis loop. This is particularly advantageous where the process of the invention is employed to upgrade an existing plant. Thus the ammonia synthesis gas generation capacity of the existing plant is increased by the use of the second stream with the addition of the pre-reforming and partial oxidation steps of the second stream and by the addition of one or more shift stages treating the reformed second stream and a pressure swing adsorption stage removing carbon dioxide and some nitrogen from the shifted second stream. If the existing plant does not have a stage of hydrogen recovery from the synthesis loop purge, such a stage may be added to enable the remainder of the excess of nitrogen in the second stream, and any excess of nitrogen in the first stream, to be separated. In this arrangement, it is preferred that the reforming conditions are such that the carbon dioxide-depleted first stream has a hydrogen to nitrogen molar ratio of 2.5 to 2.9, especially 2.7 to 2.8, and the shifted second stream has a hydrogen to nitrogen molar ratio of 1.3 to 1.7, and that the pressure swing adsorption stage removes sufficient nitrogen, in addition to carbon dioxide, that the carbon dioxide-depleted second stream has a hydrogen to nitrogen molar ratio of 1.8 to 2.5, especially 1.9 to 2.2.

As indicated above, it is preferred that a hydrogen stream is added to the second stream after the low temperature adiabatic reforming stage and before the partial oxidation stage. This hydrogen stream is conveniently derived from a purge stream taken from the loop. The loop purge stream will normally contain synthesis inerts, such as methane and argon (if air is used for the second stream partial oxidation stage and any first stream secondary reforming stage) together with unreacted synthesis reactants, i.e. hydrogen and nitrogen (in the case of ammonia synthesis) or carbon oxides (in the case of synthesis of organic compounds). Since the methane will be reacted in the second stream partial oxidation stage, it is not necessary to remove this from the purge stream in the production of the desired hydrogen stream. However, unless there is another treatment step removing any excess of loop reactants, e.g. nitrogen, or other loop inerts, e.g. argon, it is desirable to subject that loop purge to an appropriate separation step and/or only use part of the loop purge as the hydrogen stream fed into the second stream processing.

The second stream treatment units, i.e. low temperature adiabatic reforming and partial oxidation units, together with the associated equipment such as a compressor for the oxygen-containing gas used in the partial oxidation stage, any fired heater, and cooling equipment, and, in the aforementioned variant, the shift reactor and pressure swing adsorption equipment can be constructed as a stand-alone modular unit and installed to increase the capacity of an existing plant by simply connecting in parallel with the existing first stream primary reformer (and secondary reformer if used). It is seen that the minimum of intrusion into the existing plant is necessary to effect installation. Likewise, in operation, the second stream processing stages can be shut down without shutting down the first stream processing.

In addition to the production of ammonia synthesis gas, as mentioned above, the invention is of particular utility in the production of methanol synthesis gas. In processes wherein there is no bypass of the primary reformer, the primary reforming step is usually operated using a relatively high steam ratio, e.g. above 3, typically 3.0 to 3.5, a relatively low pressure, e.g. 10-30 bar abs, and a relatively high reformer outlet temperature, usually above 800° C., e.g. 850°-880° C. in order that the reformed gas has a relatively low methane content, typically below 3% by volume on a dry basis. With a feedstock such as natural gas, such conditions give a gas containing more hydrogen than is required for methanol synthesis. Thus, with a natural gas feedstock, the parameter "R" is significantly above the value of 2 which represents the stoichiometric composition for methanol synthesis. The purge gas stream from the synthesis loop enables the excess of hydrogen as well as inerts to be removed from the synthesis loop. However a relatively large purge has often to be employed.

There have been proposals to employ reforming pressures similar to the methanol synthesis pressure, and indeed there is an overlap between pressure ranges proposed for reforming and the range of pressures at which methanol synthesis can be effected. However for efficient methanol synthesis, the methanol synthesis pressure is normally somewhat higher than the maximum pressure, about 45 bar abs., at which steam reforming in tubes heated in a fired furnace is a viable proposition. The methanol synthesis pressure in a modern, low pressure, synthesis process is usually in the range 50–150 bar abs., and commonly in the range 60–120 bar abs.

Thus usually the make-up gas is produced at a lower pressure than that employed for the methanol synthesis and is compressed prior to feeding to the synthesis loop. If there is a substantial excess of hydrogen, such as results from the steam reforming of natural gas under the conventional reforming conditions, over 4 volumes of make-up gas (after drying) have to be compressed from the reforming pressure to the methanol synthesis pressure for each volume of methanol produced. Such compression necessarily consumes a significant amount of energy.

By means of the present invention, it is possible to devise a process wherein the volume of gas that has to be compressed is decreased. Thus the second stream partial oxidation stage can be operated at a higher pressure than that employed for the primary reforming of the first stream: in one embodiment of the invention the autothermal reforming stage may be effected at essentially the pressure of the synthesis loop.

Thus in a preferred form of the invention, prior to the partial oxidation stage, the second feedstock stream is compressed, the partial oxidation of the second feedstock stream is effected at a pressure greater than that at which the primary reforming of the firsdt stream is effected, and the primary reformed first stream is compressed prior to mixing with the cooled reformed second stream.

In accordance with the invention the methanol synthesis is effected in a synthesis loop from synthesis gas formed from a mixture of make-up gas and recycle gas at an elevated synthesis pressure, and synthesised methanol is separated to give a stream of unreacted gas, part of which is recycled as said recycle gas. Part of the make-up gas is obtained by steam reforming a desulphurised first hydrocarbon feedstock stream at an elevated reforming pressure that is below said synthesis pressure followed by cooling, water removal and compression to said synthesis pressure. A stream of gas is taken from the methanol synthesis loop from a point between, in flow direction, the step of separation of the synthesised methanol and the step of methanol synthesis, and this stream taken from the loop is used as the hydrogen-containing stream that is mixed with the product of the low temperature adiabatic reforming of the second desulphurised hydrocarbon feedstock stream at a pressure above the aforesaid reforming pressure, and the resulting mixture is subjected to partial oxidation with a stream of oxygen to give a hot reformed second stream which is then cooled and returned to the synthesis loop as the remainder of the make-up gas.

For convenience the stream of gas taken from the loop is herein referred to as the ex-loop gas. Circulation of the gas round the synthesis loop is normally effected by a circulator. The circulator is normally located between, in the flow direction, the step of methanol separation and the step of methanol synthesis and serves to compress the unreacted gas from the methanol separator back to the synthesis pressure. The make-up gas may be added to the loop before or after the circulator. In one embodiment of the invention, part of the gas from the circulator outlet, i.e. at the synthesis pressure, is taken as the ex-loop gas stream added to the second feedstock stream fed to the partial oxidation stage and the cooled product from the partial oxidation stage is returned to the synthesis loop at the circulator inlet. In this case the second stream partial oxidation stage is effected at essentially the synthesis pressure. In this case it is necessary that the second feedstock stream, and the oxygen, is compressed to about the synthesis pressure before addition to the partial oxidation stage, but the volume of gas that has to be so compressed is far less than if the second feedstock stream had first been subjected to conventional primary steam reforming. In an alternative embodiment, where a multistage compression of the make-up gas is employed, and particularly where the circulator is unable to handle the additional amount of gas resulting from the partial oxidation stage, the ex-loop gas mixed with the second feedstock stream and fed to the partial oxidation stage may be taken from before or after the circulator and the product from the second stream partial oxidation stage returned to the loop by addition to the make-up gas between compression stages.

The pressure at which the low temperature adiabatic reforming stage is operated is preferably about the same as that employed for the partial oxidation step so that no compression of the pre-reformed gas between pre-reforming and the partial oxidation step is necessary.

The ex-loop stream is added to the compressed additional feedstock stream after the pre-reforming and any adiabatic reforming stages.

In the second stream partial oxidation stage of this embodiment of the invention, the product of low temperature adiabatic reforming of the second hydrocarbon stream, together with the ex-loop gas, is fed to the partial oxidation stage wherein the mixture is partially combusted with oxygen and then passed through a steam reforming catalyst. In a variation of this process, the partial oxidation may be non-catalytic, i.e. the steam reforming catalyst may be omitted, and the partial oxidation may be effected essentially in the absence of steam. In some cases, particularly where a non-catalytic partial oxidation step is employed, it may be possible to omit the low temperature adiabatic reforming step, so that the second feedstock stream and ex-loop gas is fed directly to the partial oxidation stage. In either embodiment the product from the partial oxidation stage is cooled and returned to the loop together with the make-up gas from the primary reformer.

Thus the present invention also provides a process for the production of methanol in a synthesis loop wherein methanol is synthesised from synthesis gas formed from a mixture of make-up gas and recycle gas at an elevated synthesis pressure, and synthesised methanol is separated to give a stream of unreacted gas, part of which is recycled as said recycle gas, said make-up gas being obtained by steam reforming a desulphurised hydrocarbon feedstock at an elevated reforming pressure that is below said synthesis pressure followed by cooling, water removal and compression to said synthesis pressure, and is characterised in that a stream of gas is taken from said methanol synthesis loop from a point between, in flow direction, the step of separation of the synthesised methanol and the step of methanol synthesis, and this stream taken from the loop is mixed with a further quantity of desulphurised hydrocarbon feedstock at a pressure above said reforming pressure, the resulting mixture is reacted adiabatically with a stream of oxygen to give a hot gas stream which is then cooled and returned to the synthesis loop.

As indicated hereinbefore, a purge is desirably taken from the loop, before or after addition of the make-up gas and before or after taking the aforesaid ex-loop gas from the loop. The purge is normally taken from a point between the step of methanol separation and the circulator inlet. This purge is required to avoid build up of unreacted methane and inerts such as nitrogen which may be present in the feedstock, e.g. where the latter is natural gas, and/or in the oxygen stream. This purge may be used as fuel for a gas turbine driving a generator or air compressor and/or for other heating purposes, e.g. feedstock preheating prior to the partial oxidation. The air used for the combustion firing the primary reformer may be the hot exhaust from such a gas turbine.

Preferably the amount of oxygen employed is such that the gas added to the loop, i.e. the partial oxidation product plus the make-up gas from the primary reforming stage, has an "R" value in the range 1.8 to 2.5.

As indicated hereinbefore, as a result of the use of higher pressures, lower temperatures, and, possibly, lower steam ratios than is conventional in the production of methanol synthesis gas by steam reforming, the methane content of the primary reformed gas will be somewhat greater than is conventional and in particular is preferably at least 5%, and particularly in the range 6-15%, by volume on a dry basis. Although this larger amount of methane is fed to the synthesis loop, the methane in the ex-loop gas fed to the partial oxidation stage augments the amount of additional feedstock fed the partial oxidation step.

Before returning the product stream from the partial oxidation step to the loop, it is cooled to an appropriate temperature, preferably below about 50° C. This is conveniently effected by heat recovery and quenching with cold water with subsequently separation of the liquid water phase prior to synthesis. The heat recovery may include steam raising and/or superheating, boiler feed water heating, and/or reactants preheating.

In order to increase the capacity of an existing plant, it may be desirable to employ an auxiliary synthesis stage wherein the reformed first or second stream, or a mixture of both reformed streams, is subjected to an auxiliary methanol synthesis stage at an intermediate pressure, i.e. above the pressure employed for the primary reforming step, but below the pressure employed in the synthesis stage of the synthesis loop, prior to addition of the relevant stream to the synthesis loop.

Thus in one form of the invention, the product from the partial oxidation step is passed, without further compression, to an auxiliary methanol synthesis reactor to synthesise some methanol. This synthesised methanol may be separated in a catchpot and then the unreacted gas from this catchpot returned to the loop. In another embodiment, where the primary reformed gas is compressed in more than one stage before addition to the loop, the primary reformed gas between those compression stages may be passed to an auxiliary methanol synthesis reactor to synthesise some methanol from both the partial oxidation product and the make-up gas. After cooling, the synthesised methanol is then separated in, for example, the compressor inter-stage condensate separator, and the unreacted gas from this separator is fed to the next compression stage and then to the loop. Alternatively the reformed second stream, i.e. partial oxidation product, may be added to the partially compressed primary reformed gas between compression stages and the resulting mixture fed to the auxiliary synthesis stage.

In another embodiment the partial oxidation product, after being subjected to methanol synthesis in an auxiliary reactor, is returned to the loop between the main synthesis reactor and the methanol separator. In this case the loop methanol separator serves to separate the methanol produced in both the loop synthesis stage and the auxiliary methanol synthesis stage.

Where an auxiliary reactor is employed, the pressure of the gas entering the auxiliary synthesis reactor is preferably in the range 40-80 bar abs. and the loop synthesis pressure is higher, preferably in the range 50-100 bar abs. It is often desirable to employ predominantly isothermal conditions in the auxiliary reactor. Suitable reactor designs are described in EP 80270 and EP 81948.

The feed to the synthesis reactor or reactors should be heated as necessary to adjust the synthesis inlet temperature to the desired level, usually in the range 150°-250° C.; often heat exchange with the effluent from the synthesis reactor may be employed. The catalysts employed for methanol synthesis may be any of those normally used, for example a copper/zinc oxide/alumina catalyst.

BRIEF DESCRIPTION OF THE DRAWINGS

In the drawings

In FIG. 1, the dashed lines indicate the first embodiment, while the dotted lines indicate the second embodiment.

DESCRIPTION OF SPECIFIC EMBODIMENTS.

Figure 1:
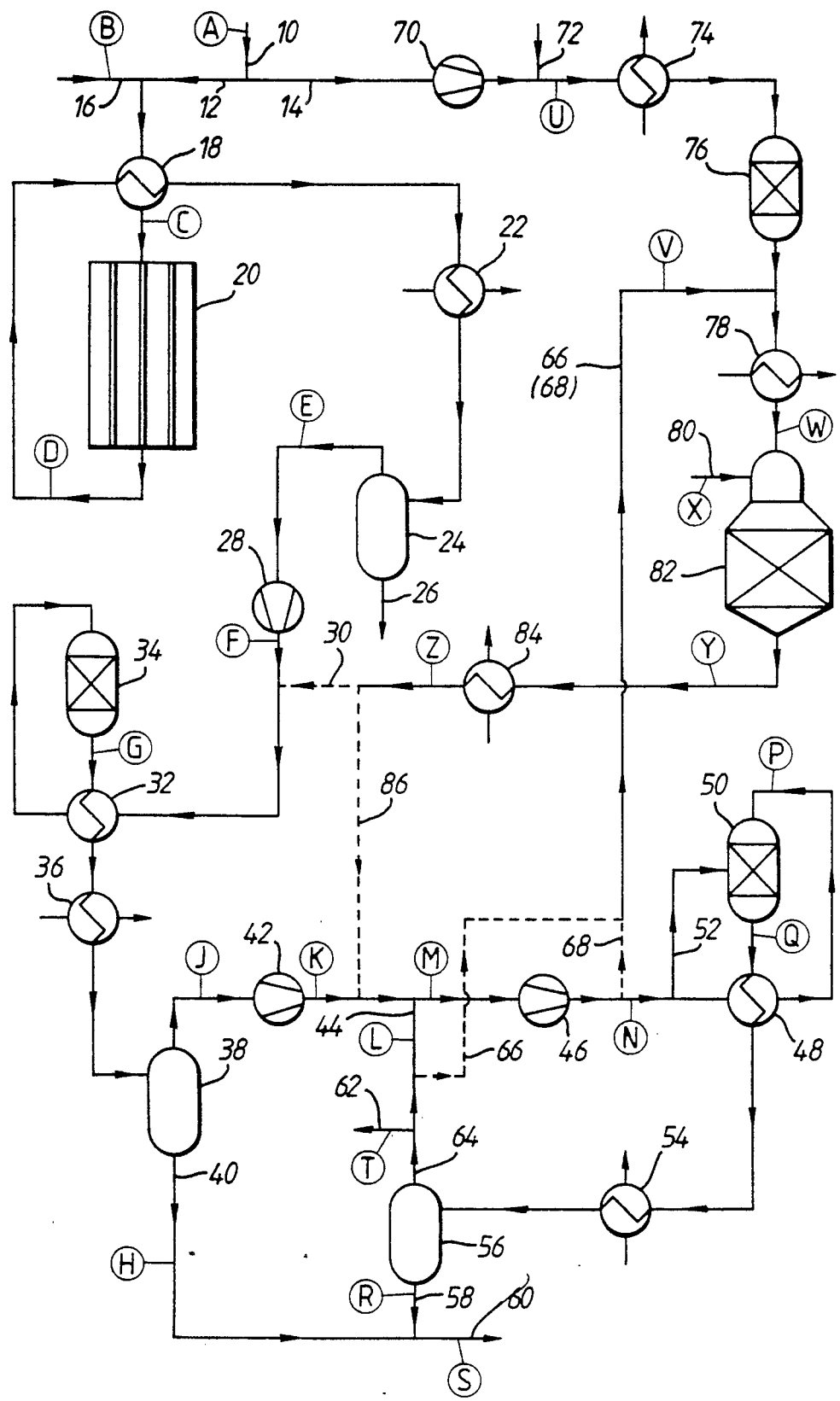
FIG. 1 is a diagrammatic flowsheet showing two embodiments of the invention for the production of methanol.

Referring to FIG. 1, in both embodiments a desulphurised feedstock stream A fed via line 10 at a pressure of e.g. 30-40 bar abs. is divided into two streams 12 and 14. Steam B is added to stream 12 via line 16 and the mixture heated in a feed/effluent heat exchanger 18 and then the heated mixture C is fed to a conventional primary steam reformer 20 containing a steam reforming catalyst, e.g. nickel on a calcium aluminate support, disposed in the reforming tubes. The reformed gas D is cooled, with heat recovery in heat exchangers 18 and 22, and then fed to a catchpot 24 wherein the excess of steam is separated as water stream 26 for recycle to a boiler (not shown). The resultant make-up gas E is then fed to the first stage 28 of a make-up gas compressor where it is compressed to an intermediate pressure, for example about 50 bar abs., giving compressed make-up gas F.

In the first embodiment the make-up gas F is then mixed with cooled autothermally reformed gas Z (described below) supplied via line 30 and passed through a feed/effluent heat exchanger 32. In heat exchanger 32 the gas is heated to a suitable temperature, e.g. 150° to 250° C., for entry into an auxiliary methanol synthesis converter 34 containing a copper/zinc oxide/alumina methanol synthesis catalyst. Converter 34 is maintained under essentially isothermal conditions by cooling the catalyst bed with water passing through tubes (not shown) immersed in the bed and under such pressure that the water boils raising steam. Methanol is synthesised from the mixture of make-up gas and autothermally reformed gas and the effluent G from the auxiliary converter 34 is used as the heating medium in heat exchanger 32. The effluent is then cooled further by the make-gas compressor inter-stage cooler 36 and fed to the make-up gas interstage catchpot 38 wherein methanol and water are separated as auxiliary product stream E via line 40. The remaining gas J is then passed to the final stage 42 of the make-up gas compressor wherein it is compressed to the loop circulator inlet pressure.

In the second embodiment no autothermally reformed gas is added to the make-up gas F between the compression stages.

In both embodiments, the make-up gas K from the second compression stage 42 is then mixed with recycle gas L supplied via line 44 and the mixture M is fed to circulator 46 where it is compressed to the loop synthesis pressure, e.g. 80 to 100 bar abs. The resultant synthesis gas N at the loop synthesis pressure is then fed to a feed/effluent heat exchanger 48 where the mixture is heated to the synthesis inlet temperature. The heated synthesis gas P is then fed to the loop synthesis converter 50 wherein methanol is synthesised using a copper/zinc oxide/alumina catalyst. This converter may be of the quench reactor or the tube-cooled type. When using a quench reactor, a suitable supply of quench gas may be taken via line 52 from the synthesis gas N prior to heat exchanger 48. The effluent reacted gas Q from the loop converter 50 is used as the heating medium in heat exchanger 48 and is then fed to a cooler 54 wherein heat is recovered, e.g. for use in distillation of crude methanol. The cooled reacted gas is then passed to separator 56 wherein the main product methanol/water stream R is separated via line 58 and may be mixed with stream H from the auxiliary synthesis stage separator 38 to give a product S delivered to line 60. A purge stream T is taken via line 62 from the unreacted gas stream 64 leaving separator 56. The remaining unreacted gas L forms the recycle gas in line 44.

In the first embodiment a part stream of the unreacted gas is taken as the ex-loop gas stream via line 66 from upstream of the circulator 46. It may be taken, as shown in FIG. 1, from line 44, i.e. before addition of the make-up gas K from the second stage 42 of the make-up gas compressor. Alternatively it may be taken from the circulator inlet, i.e. after mixing the make-up gas K with the recycle gas L from line 44. In the second embodiment the ex-loop gas stream is taken, via line 68, from the circulator product stream N.

In either embodiment, the second stream 14 of desulphurised feedstock is fed to a compressor 70 wherein it is compressed and then mixed with steam supplied via line 72. The steam/feedstock mixture U is then heated in a fired heater 74 to about 550° C. and passed through an adiabatic pre-reformer 76 containing a bed of low temperature steam reforming catalyst, e.g. a nickel based CRG catalyst. The resultant pre-reformed gas, at a temperature of for example about 500° C., is then mixed with the ex-loop gas stream V, i.e. stream 66 in the first embodiment or stream 68 in the second embodiment. The gas mixture is then heated further, e.g. to 650° C. in a fired heater 78. Heaters 74 and 78 may be heated by combustion of the loop purge T. The heated gas mixture W from heater 78 is then autothermally reformed with oxygen X supplied via line 80 in an autothermal reformer 82 containing a nickel on a refractory support steam reforming catalyst. The autothermally reformed gas Y is then cooled with heat recovery, e.g. steam raising, in heat exchanger 84, to give a cooled autothermally reformed stream Z.

In the first embodiment the cooled autothermally reformed gas Z is fed via line 30 to be united with the make-up gas F before feeding the latter to heat exchanger 32 and auxiliary synthesis reactor 34.

In the second embodiment the cooled autothermally reformed gas Z is fed via line 86 to the loop. It may be added to the loop recycle stream 44, or to the circulator 46 inlet, or, as shown, to the compressed make-up gas from the second stage 42 of the make-up gas compressor.

As described above, the product Z of processing the second feedstock stream 14 in the pre-reforming and autothermal reforming stages 76 and 82 is added to the primary reformed gas stream between compression stages 28 and 42 in the first embodiment, or directly to the loop in the second embodiment. The pressure to which the second feedstock stream is compressed in compressor 70 should thus be sufficient that, after the subsequent processing of that second feedstock stream, it is at a pressure suitable for addition to the partly compressed make-up gas (in the first embodiment) or to the loop (in the second embodiment). Thus in the first embodiment second feedstock stream 14 is compressed in compressor 70 to a pressure sufficiently above that of the delivery pressure, which is about 50 bar abs., of the first stage 28 of the make-up gas compressor to allow for the inevitable pressure drop occuring on passage through reformers 76 and 82. Likewise, in the second embodiment, the second feedstock stream 14 is compressed to a pressure sufficiently above the loop circulator inlet pressure to allow for the pressure drops in reformers 76 and 82.

Figure 2:
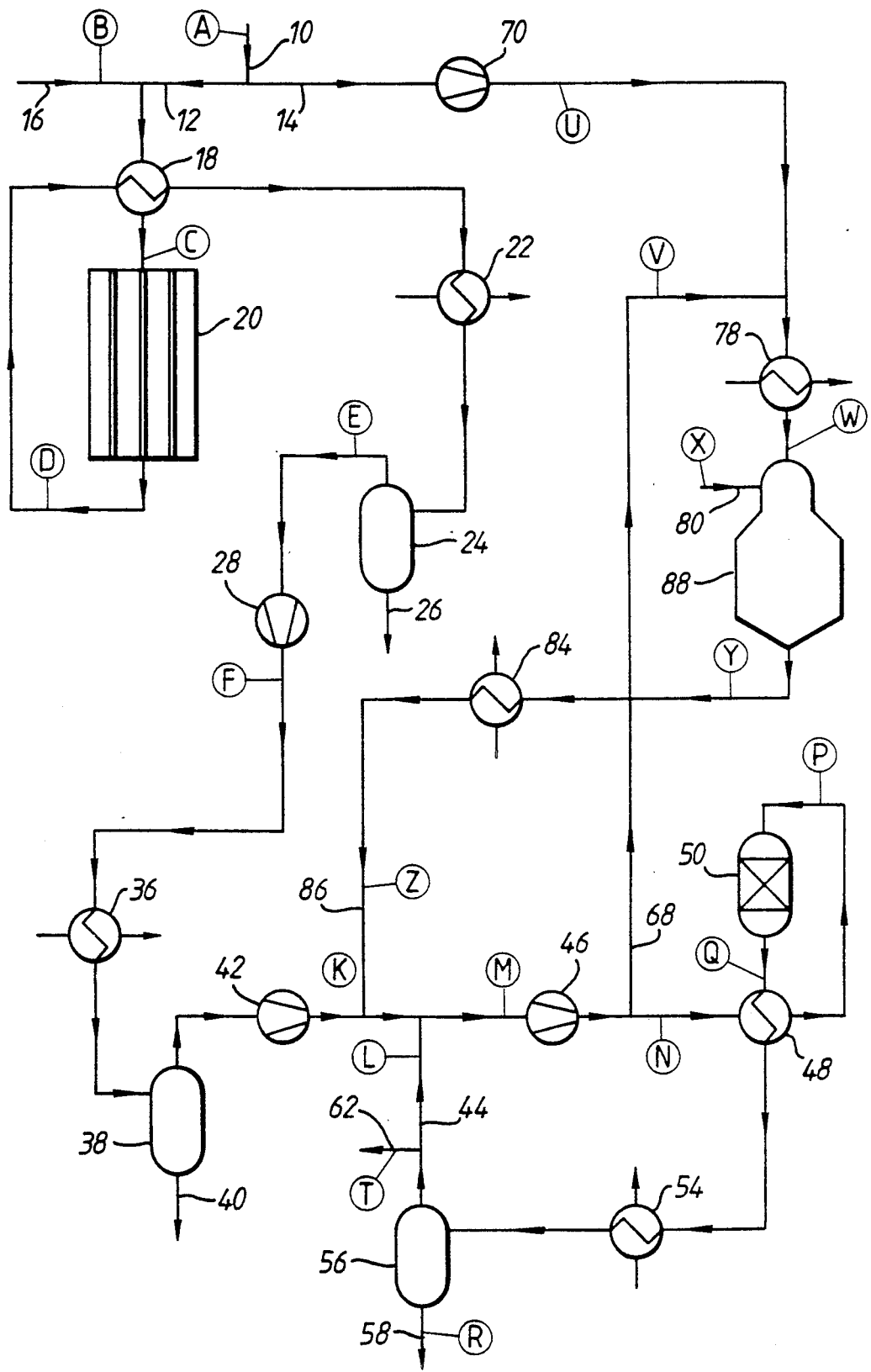
FIG. 2 is a flowsheet similar to that of FIG. 1 but showing a simplified embodiment.

FIG. 2 shows a variant of the second embodiment of FIG. 1. In this variant, the heat exchanger 32 and the auxiliary converter 34 are omitted so that the make-up gas F passes in conventional fashion from the first stage 28 of the make-up gas compressor to the inter-stage cooler 36. In this instance of course there will be no methanol in the stream 40 separated in the inter-stage catchpot 38 and so here stream 40 is not combined with the product R in line 58. In this variant a single stage make-up gas compressor may be employed and cooler 36, catchpot 38, and second stage compressor 42 omitted. Also in this variant shown in FIG. 2, the autothermal reformer 82 of FIG. 1 is replaced by a non-catalytic partial oxidation unit 88. In this case, the steam supply 72, heater 74, and pre-reformer 76 of the FIG. 1 embodiment are omitted. It will be appreciated that the first embodiment of FIG. 1 could likewise be modified to employ non-catalytic partial oxidation in place of autothermal reforming (again with the omission of steam supply 72, heater 74, and pre-reformer 76).

In Table 1 below, calculated gas compositions (quoted to the nearest whole percentage), temperatures, and flow rates (quoted to the nearest kmol/h) are shown at the various stages of a process in accordance with the flowsheet of FIG. 2. For simplicity it has been assumed that the desulphurised feedstock is 100% methane and the oxygen is pure. In practice, if desulphurised natural gas is used as the feedstock, it will contain a small proportion of higher hydrocarbons, and possibly nitrogen, carbon dioxide, and hydrogen, while the oxygen stream will normally contain a small proportion of nitrogen. The calculations assume that the primary reforming is effected at 30 bar abs., the loop is at 80 bar abs., and the partial oxidation is effected at 80 bar abs. Assuming that the feedstock and oxygen are available at 30 bar abs., calculated power requirements are also shown in Table 1.

former 20 and the heat exchanger 18. The autothermally reformed gas Y from autothermal reformer 82 is cooled, with heat recovery, in heat exchanger 90 before being used to heat the feedstock/steam mixture in heat exchanger 18. The second stream 14 of desulphurised feedstock, is heated in heater 78, to give a heated second stream U and mixed with the primary reformed gas D before entry into the autothermal reformer. In this case it is assumed that the primary and autothermal reforming are effected at 30 bar abs., with the loop again operating at 80 bar abs.

TABLE 2

| Stream | Temp (°C.) | Stream composition (% v/v) | | | | | | | Total flow kmol/h |
|---|---|---|---|---|---|---|---|---|---|
| | | CH$_4$ | H$_2$O | O$_2$ | CO | CO$_2$ | H$_2$ | CH$_3$OH | |
| A | 20 | 100 | 0 | 0 | 0 | 0 | 0 | 0 | 100 |
| B | 278 | 0 | 100 | 0 | 0 | 0 | 0 | 0 | 180 |
| C | 500 | 25 | 75 | 0 | 0 | 0 | 0 | 0 | 240 |
| D | 710 | 13 | 49 | 0 | 2 | 6 | 30 | 0 | 287 |
| U | 500 | 100 | 0 | 0 | 0 | 0 | 0 | 0 | 40 |
| X | 200 | 0 | 0 | 100 | 0 | 0 | 0 | 0 | 48 |
| Y | 980 | 1 | 32 | 0 | 14 | 6 | 47 | 0 | 472 |
| K | 66 | 1 | 0 | 0 | 21 | 9 | 69 | 0 | 320 |
| P | 240 | 11 | 0 | 0 | 9 | 8 | 71 | 0 | 1442 |
| Q | 270 | 13 | 2 | 0 | 5 | 7 | 66 | 8 | 1264 |
| R | 40 | 0 | 20 | 0 | 0 | 3 | 1 | 76 | 117 |
| T | 40 | 14 | 0 | 0 | 5 | 8 | 72 | 1 | 25 |
| L | 40 | 14 | 0 | 0 | 5 | 8 | 72 | 1 | 1121 |

| | Power requirements (kW) |
|---|---|
| Make-up gas compression | 411 |
| Circulator | 116 |
| CH$_4$ + O$_2$ compression | — |

Calculation shows that the cooling requirements for cooling the reformed gas stream D and the autothermally reformed gas Y of Table 1 from the respective outlet temperature of 830° C. and 1150° C. to 100° C. are almost identical with the requirements for cooling the autothermally reformed gas Y of Table 2 from its outlet temperature of 980° C. to 100° C.

To illustrate the benefits of the use of an auxiliary

TABLE 1

| Stream | Temp (°C.) | Stream composition (% v/v) | | | | | | | Total flow kmol/h |
|---|---|---|---|---|---|---|---|---|---|
| | | CH$_4$ | H$_2$O | O$_2$ | CO | CO$_2$ | H$_2$ | CH$_3$OH | |
| A | 20 | 100 | 0 | 0 | 0 | 0 | 0 | 0 | 100 |
| B | 278 | 0 | 100 | 0 | 0 | 0 | 0 | 0 | 100 |
| C | 500 | 25 | 75 | 0 | 0 | 0 | 0 | 0 | 133 |
| D | 830 | 6 | 37 | 0 | 7 | 6 | 44 | 0 | 180 |
| K | 66 | 9 | 0 | 0 | 12 | 9 | 70 | 0 | 113 |
| U | 39 | 100 | 0 | 0 | 0 | 0 | 0 | 0 | 67 |
| V | 41 | 35 | 0 | 0 | 9 | 3 | 53 | 1 | 117 |
| W | 640 | 58 | 0 | 0 | 5 | 2 | 34 | 0 | 184 |
| X | 250 | 0 | 0 | 100 | 0 | 0 | 0 | 0 | 46 |
| Y | 1150 | 12 | 7 | 0 | 24 | 1 | 55 | 0 | 322 |
| P | 240 | 35 | 0 | 0 | 9 | 3 | 53 | 1 | 2367 |
| Q | 270 | 38 | 0 | 0 | 6 | 3 | 49 | 5 | 2188 |
| R | 40 | 2 | 9 | 0 | 0 | 1 | 1 | 87 | 103 |
| T | 40 | 39 | 0 | 0 | 6 | 3 | 51 | 1 | 15 |
| L | 40 | 39 | 0 | 0 | 6 | 3 | 51 | 1 | 2071 |

| | Power requirements (kW) |
|---|---|
| Make-up gas compression | 137 |
| Circulator | 200 |
| CH$_4$ + O$_2$ compression | 101 |

Figure 3:
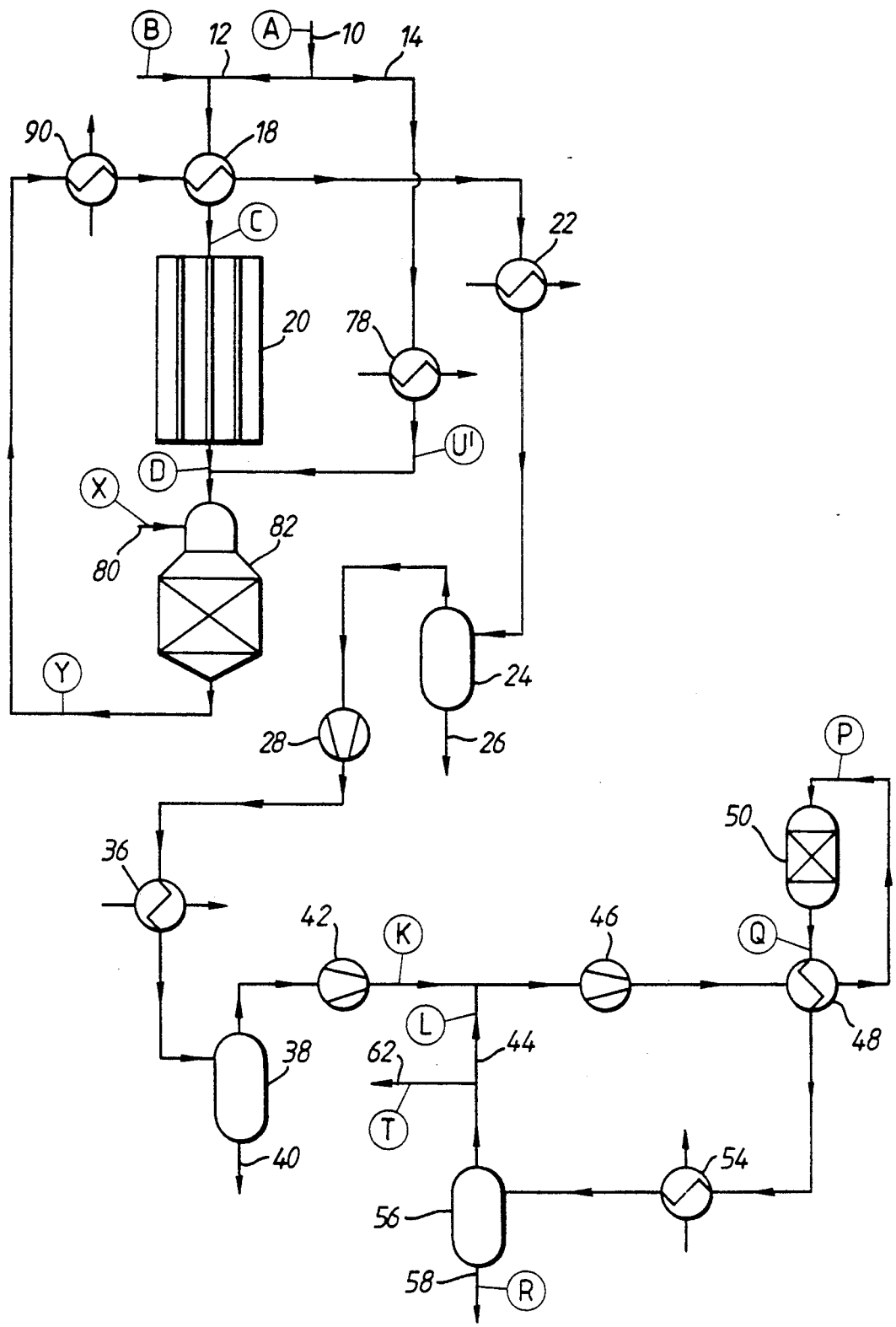
FIG. 3 is a flowsheet of a prior art process for the purposes of comparison.

For purposes of comparison, similar details are shown in Table 2 below for the production of the approximately the same amount (89 kmol/h) of methanol from the same amount (100 kmol/h) of feedstock using the prior art flowsheet of FIG. 3. In this arrangement a catalytic autothermal reformer 82 and a further heat exchanger 90 are interposed between the primary resynthesis stage, the following calculated example employs a simplified version of the flowsheet shown in FIG. 1. In this simplification the bypass stream 14 and its associated treatment steps are omitted. Thus all the feedstock is fed to the heat exchanger 18 and then as stream C to the conventional primary reformer 20. The primary reformed gas D is cooled, and water removed, to give the make-up gas E fed to the first compression stage 28. The compressed gas F is then passed to the auxiliary methanol synthesis stage 34 via heat exchanger 32 and, after cooling, the synthesised methanol H is separated in catchpot 38 before the unreacted gas J is compressed in the second compressor stage 42 and fed, together with loop recycle L, to the loop circulator. No stream 66 or 68 is taken from the loop.

In this calculated example, methane at 20 bar abs. is used as the feedstock, and the auxiliary and loop synthesis steps are effected at about 40 and 100 bar abs. respectively. The temperature (T), pressure (P), composition, and flow rate of the streams at various stages of the process are shown in the following Table 3.

TABLE 3

| | (P) bar abs | (T) °C. | Stream composition (% v/v) | | | | | | Total flow kmol/h |
|---|---|---|---|---|---|---|---|---|---|
| | | | CH$_4$ | CO | CO$_2$ | H$_2$ | H$_2$O | MeOH | |
| C | 20 | 500 | 25.0 | | | 75.0 | | | 400.0 |
| D | | 880 | 2.1 | 10.3 | 5.0 | 50.8 | 31.8 | | 576.1 |
| E | 17 | 50 | 3.0 | 15.0 | 7.3 | 74.2 | 0.5 | | 394.7 |
| F | 41 | 151 | 3.0 | 15.0 | 7.3 | 74.2 | 0.5 | | 394.7 |
| G | | 260 | 3.4 | 10.5 | 8.0 | 70.4 | 0.8 | 6.9 | 346.8 |
| H | 38 | 40 | 0.1 | 0.1 | 2.0 | 0.5 | 10.6 | 86.7 | 23.7 |
| J | 38 | 40 | 3.7 | 11.2 | 8.4 | 75.5 | 0.1 | 1.0 | 323.1 |
| K | 91 | 149 | 3.7 | 11.2 | 8.4 | 75.5 | 0.1 | 1.0 | 323.1 |
| M | 91 | 65 | 8.7 | 3.6 | 3.2 | 83.8 | 0.1 | 0.6 | 1469.9 |
| N | 100 | 76 | 8.7 | 3.6 | 3.2 | 83.8 | 0.1 | 0.6 | 1469.9 |
| P | 100 | 240 | 8.7 | 3.6 | 3.2 | 83.8 | 0.1 | 0.6 | 1469.9 |
| Q | | 270 | 9.4 | 1.4 | 1.6 | 80.6 | 1.9 | 5.0 | 1351.2 |
| R | 91 | 40 | 0.3 | 0.0 | 0.7 | 0.9 | 28.1 | 70.0 | 88.8 |
| T | 91 | 40 | 10.1 | 1.5 | 1.7 | 86.2 | 0.1 | 0.5 | 115.6 |
| L | 91 | 40 | 10.1 | 1.5 | 1.7 | 86.2 | 0.1 | 0.5 | 1146.9 |
| S | | 40 | 0.3 | 0.0 | 0.9 | 0.8 | 24.4 | 73.5 | 112.5 |

For purposes of comparison Table 4 sets out the corresponding parameters for a conventional process employing the same amount of feedstock and giving the same amount (82.75 kmol/h) of product methanol. In this conventional process, heat exchanger 32 and auxiliary synthesis reactor 34 are omitted so that the gas F from the first compression stage passes directly to cooler 36. In this case, since there is no heat exchanger 32 and auxiliary reactor 34, the pressure drop between the outlet of the first compression stage 28 and the inlet to the second compression stage 42 is decreased. In this case, the product is simply the stream R separated from the loop and does not include the water separated from the gas between the first and second compression stages.

TABLE 4

| | (P) bar abs | (T) °C. | Stream composition (% v/v) | | | | | | Total flow kmol/h |
|---|---|---|---|---|---|---|---|---|---|
| | | | CH$_4$ | CO | CO$_2$ | H$_2$ | H$_2$O | MeOH | |
| C | 20 | 500 | 25.0 | | | 75.0 | | | 400.0 |
| D | | 880 | 2.1 | 10.3 | 5.0 | 50.8 | 31.8 | | 576.1 |
| E | 17 | 50 | 3.0 | 15.0 | 7.3 | 74.2 | 0.5 | | 394.7 |
| F | 40 | 147 | 3.0 | 15.0 | 7.3 | 74.2 | 0.5 | | 394.7 |
| J | 39 | 40 | 3.0 | 15.1 | 7.3 | 74.4 | 0.2 | | 393.7 |
| K | 91 | 147 | 3.0 | 15.1 | 7.3 | 74.4 | 0.2 | | 393.7 |
| M | 91 | 64 | 8.5 | 4.6 | 3.0 | 83.4 | 0.1 | 0.4 | 1771.8 |
| N | 100 | 75 | 8.5 | 4.6 | 3.0 | 83.4 | 0.1 | 0.4 | 1771.8 |
| P | 100 | 240 | 8.5 | 4.6 | 3.0 | 83.4 | 0.1 | 0.4 | 1771.8 |
| Q | | 270 | 9.4 | 1.5 | 1.7 | 80.1 | 1.7 | 5.6 | 1605.2 |
| R | 91 | 40 | 0.3 | 0.0 | 0.7 | 1.0 | 23.9 | 74.0 | 111.8 |
| T | 91 | 40 | 10.0 | 1.7 | 1.7 | 86.0 | 0.1 | 0.5 | 115.3 |
| L | 91 | 40 | 10.0 | 1.7 | 1.7 | 86.0 | 0.1 | 0.5 | 1378.1 |

Calculated power requirements for the first and second compression stages and for the circulator for both processes are set out in Table 5. These calculations assume that in each case the pressure ratios in the first and second compression stages are the same and that the first and second stage compressors, and the circulator, have a polytropic efficiency of 80%.

TABLE 5

| | Power required (kW) | |
|---|---|---|
| Compressor | Auxiliary synth. | No auxiliary synth. |
| First stage | 367 | 356 |
| Second stage | 302 | 358 |
| Circulator | 143 | 172 |
| Total | 812 | 886 |

It is thus seen that in this example the use of an auxiliary synthesis step results in a compression power saving of about 8%.

It is thus seen that significant benefits could be obtained by the use of such an auxiliary synthesis step in the process of the invention, i.e. where part of the feedstock bypasses the primary reformer and is mixed with gas taken from the loop and the mixture subjected to a partial oxidation stage.

Figure 4:
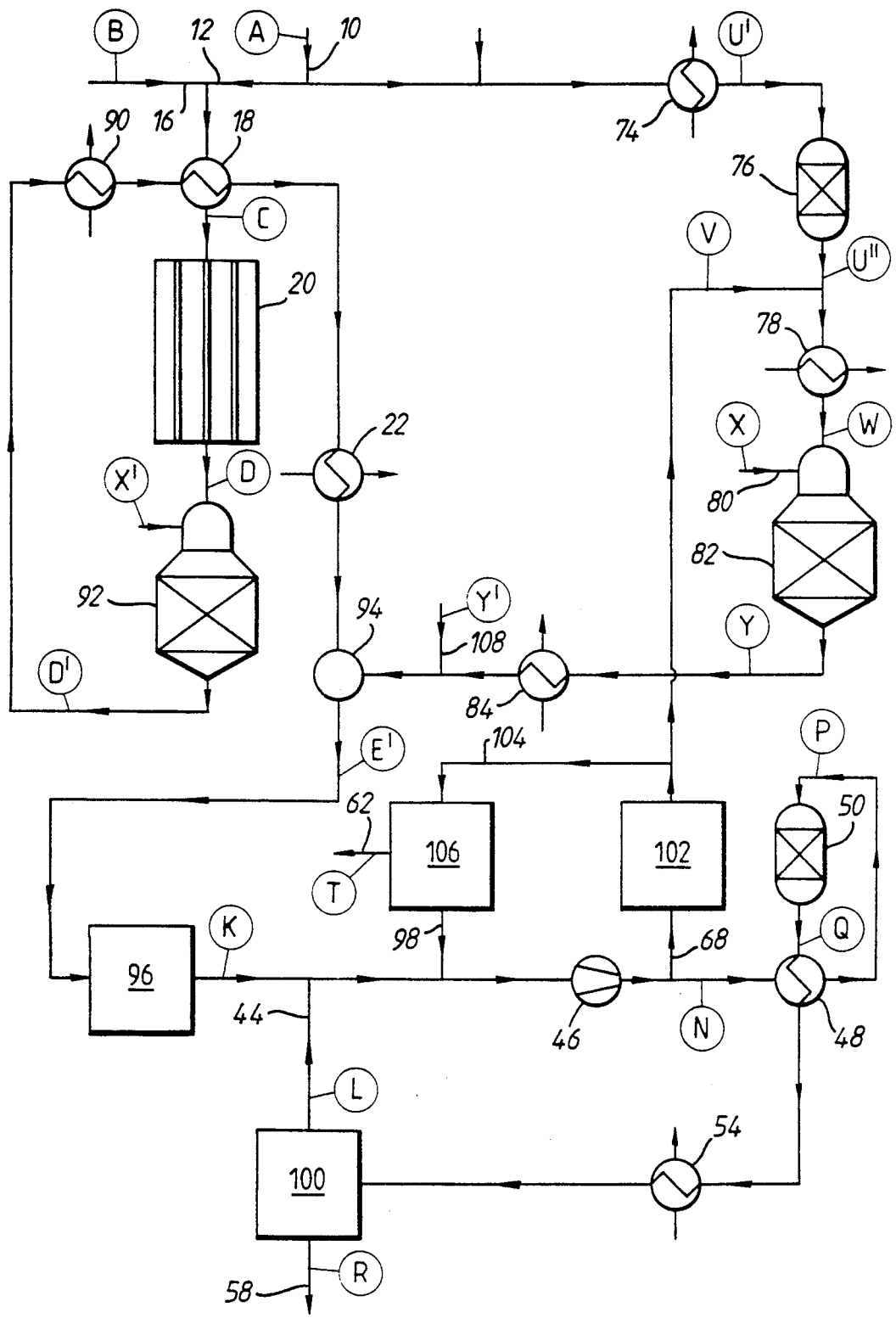
FIG. 4 is a flowsheet of the process applied to the production of ammonia.

In the embodiment of FIG. 4, the synthesis of ammonia is shown. In this embodiment a desulphurised feedstock stream A is fed via line 10 at a pressure of e.g. 30-40 bar abs. is divided into two streams 12 and 14. Steam B is added to stream 12 via line 16 and the mixture heated in a feed/effluent heat exchanger 18 and then fed as stream C to a conventional primary steam reformer 20 containing a steam reforming catalyst, e.g. nickel on a calcium aluminate support, disposed in the reforming tubes. The primary reformed gas D is then fed to a secondary reformer 92 where it is partially combusted with a stream of air X' and passed through a secondary steam reforming catalyst bed. The resultant secondary reformed gas D' is then cooled, with heat recovery in heat exchangers 90, 18 and 22, and then fed to a mixer 94 wherein it is mixed with cooled reformed second stream Z (to be described). The resulting mixture E' is then subjected to one or more stages of shift, steam and carbon dioxide removal, methanation, compression, and drying. This further processing of the mixture is depicted generally by box 96. The resultant compressed make-up gas K is then mixed with recovered hydrogen (to be described) supplied via line 98 and recycle gas L supplied via line 44, and fed to circulator 46 where it is compressed to the loop synthesis pressure, e.g. 80 to 100 bar abs. The resultant synthesis gas N at the loop synthesis pressure is then fed to a feed/effluent heat exchanger 48 where the mixture is heated to the synthesis inlet temperature. The heated synthesis gas P is then fed to the loop synthesis converter 50 wherein ammonia is synthesised using a potassium-promoted iron ammonia synthesis catalyst. This converter may be of the quench reactor or the tube-cooled type. The effluent reacted gas Q from the loop converter 50 is used as the heating medium in heat exchanger 48 and is then fed to a cooler 54 wherein heat is recovered. The cooled reacted synthesis gas is then passed to a chiller/separator 100 wherein synthesised ammonia condenses and is separated product stream R delivered via line 58. The remaining unreacted gas forms the recycle gas L in line 44.

A part stream of gas is taken from the circulator outlet via line 68, and is fed to an ammonia scrubber generally depicted by box 102. The scrubbed ex-loop gas is then divided into two. One stream is fed via line 104 to a cryogenic hydrogen recovery unit 106 where a waste gas stream, containing the excess of nitrogen, the addition of a water stream Y'. The resultant mixture Z is then fed to the mixer 94.

TABLE 6

| Stream | Temp °C. | Flow rate (kmol/h) | | | | | | | |
|---|---|---|---|---|---|---|---|---|---|
| | | Nap | CH$_4$ | CO | CO$_2$ | H$_2$ | N$_2$ | O$_2$ | Ar | H$_2$O |
| C | 460 | 270 | 0 | 0 | 0 | 0 | 0 | 0 | 0 | 6048 |
| D | 800 | 0 | 413 | 711 | 766 | 3577 | 0 | 0 | 0 | 3805 |
| X' | 480 | 0 | 0 | 0 | 1 | 0 | 1370 | 369 | 16 | 0 |
| D' | 970 | 0 | 16 | 1148 | 727 | 3990 | 1370 | 0 | 16 | 4186 |
| U' | 450 | 70 | 0 | 0 | 0 | 0 | 0 | 0 | 0 | 784 |
| U" | 496 | 0 | 364 | 3 | 123 | 81 | 0 | 0 | 0 | 535 |
| V | 42 | 0 | 2 | 0 | 0 | 34 | 12 | 0 | 3 | 0 |
| X | 480 | 0 | 0 | 0 | 0 | 0 | 870 | 234 | 10 | 0 |
| Y | 950 | 0 | 6 | 324 | 162 | 766 | 882 | 0 | 13 | 604 |
| Y' | 236 | 0 | 0 | 0 | 0 | 0 | 0 | 0 | 0 | 1292 |
| E' | 381 | 0 | 22 | 1472 | 889 | 4756 | 2252 | 0 | 29 | 6082 | some hydrogen, and methane, is separated via line 62 as a purge stream T leaving a hydrogen-enriched stream 20 which is returned to the loop via line 98. The use of the other part stream V of the scrubbed ex-loop gas is described below.

The second stream 14 of desulphurised feedstock is mixed with steam supplied via line 72. The steam/feedstock mixture is then heated in a fired heater 74 to give a heated mixture U' at about 550° C. and passed through an adiabatic pre-reformer 76 containing a bed of low temperature steam reforming catalyst, e.g. a nickel based CRG catalyst. The resultant pre-reformed gas U''', at a temperature of for example about 500° C., is then mixed with the other part stream V of the scrubbed ex-loop gas. The gas mixture is then heated further, e.g. to 650° C. in a fired heater 78. Heaters 74 and 78 may be heated by combustion of the purge T. The heated gas mixture W from heater 78 is then autothermally reformed with air X supplied via line 80 in an autothermal reformer 82 containing a nickel on a refractory support steam reforming catalyst. The autothermally reformed gas Y is then cooled with heat recovery, e.g. steam raising, in heat exchanger 84. A stream of cold water Y' is then added via line 108 and the resultant cooled reformed second stream Z is then fed to mixer 94.

This embodiment of the invention is illustrated by the following calculated example. The constituents of the various gas streams and the flow rates thereof are shown in Table 6 below wherein the flow rates have been quoted to the nearest whole number. The feedstock is desulphurised naphtha (which is assumed for the purposes of calculation to be a mixture of heptanes). The pressure of the primary reformer feed stream C and the air stream X' are such that the secondary reformed gas stream D' has a pressure of about 31 bar abs. The secondary reformed gas stream D', which has a hydrogen-equivalent to nitrogen molar ratio of about 3.75, is cooled to 370° C. before feeding to the mixer 94.

The second part of the desulphurised naphtha feedstock stream represents about 20% of the total feedstock. The mixture of the pre-reformed gas U''' from pre-reformer 76 and the scrubbed hydrogen-containing ex-loop gas V is heated to 640° C. before feeding as stream W to the autothermal reformer 82. The pre-reforming and autothermal reforming steps producing stream Y are conducted at such a pressure that stream Y has a pressure of about 32 bar abs. The secondary reformed gas stream Y leaving the autothermal reformer at 950° C. is cooled to 510° C. with heat recovery in heat exchanger 84 and then cooled further to 410° C. by In Tables 7 to 9 below, calculated flow rates (quoted to the nearest kmol/h), temperatures, and pressures are shown at the various stages of processes in accordance with the flowsheet of FIG. 1 or modifications thereof. In these examples, it is assumed that the feedstock is natural gas and the oxygen is pure. In addition to methane, the natural gas contains some higher hydrocarbons: the calculations assume that the feedstock has the following molar composition:

| methane | 93.75% | ethane | 3.21% |
|---|---|---|---|
| propane | 0.40% | butane | 0.09% |
| nitrogen | 2.20% | carbon dioxide | 0.35% |

The calculations assume that the partial oxidation is non-catalytic, the primary reforming is effected at 30 bar abs., any auxiliary synthesis stage is operated at 50 bar abs., and the loop synthesis is at 80 bar abs. In the embodiments of Tables 7 and 8 the pre-reforming and partial oxidation is effected at 80 bar abs., whereas in the Table 9 embodiment these steps are effected at 50 bar abs. In the Tables calculated power requirements are given assuming that the natural gas is available at 30 bar abs., and the oxygen is available at the pressure employed for the partial oxidation step. Streams U' and U''', which are not labelled in FIG. 1, represent the heated pre-reformer feed and the pre-reformer product respectively.

Table 7 gives the details of a process in accordance with the second embodiment of FIG. 1, i.e. with the ex-loop gas being taken from the circulator outlet via line 68 and the reformed second stream being returned directly to the loop via line 86 rather than being added to the reformed first stream before feeding to heat exchanger 32. The amount of methanol recovered in streams R and R is 90.7 kmol/h.

TABLE 7

| | Temp °C. | Pres bara | Flow rate (kmol/h) | | | | | | | |
|---|---|---|---|---|---|---|---|---|---|---|
| | | | CH$_4$ | H$_2$O | O$_2$ | N$_2$ | CO | CO$_2$ | H$_2$ | MeOH |
| A | 20 | 30 | 94* | 0 | 0 | 2 | 0 | 0 | 0 | 0 |
| C | 500 | 30 | 31* | 102 | 0 | 1 | 0 | 0 | 0 | 0 |
| D | 830 | — | 10 | 68 | 0 | 1 | 14 | 10 | 80 | 0 |
| E | 40 | — | 10 | 0 | 0 | 1 | 14 | 10 | 80 | 0 |
| F | 60 | 50 | 10 | 0 | 0 | 1 | 14 | 10 | 80 | 0 |
| G | 260 | 47 | 10 | 1 | 0 | 1 | 8 | 9 | 66 | 6 |
| H | 40 | — | 0 | 1 | 0 | 0 | 0 | 0 | 0 | 6 |
| K | 60 | 73 | 10 | 0 | 0 | 1 | 8 | 9 | 66 | 1 |
| L | 40 | 73 | 232 | 1 | 0 | 108 | 84 | 67 | 700 | 8 |
| P | 240 | 80 | 237 | 1 | 0 | 110 | 159 | 81 | 894 | 9 |
| Q | 270 | 73 | 237 | 12 | 0 | 110 | 85 | 71 | 715 | 93 |
| R | 40 | — | 1 | 11 | 0 | 0 | 0 | 2 | 1 | 85 |
| T | 40 | — | 5 | 0 | 0 | 2 | 2 | 1 | 14 | 0 |

TABLE 7-continued

| | Temp °C. | Pres bara | Flow rate (kmol/h) | | | | | | | |
|---|---|---|---|---|---|---|---|---|---|---|
| | | | CH$_4$ | H$_2$O | O$_2$ | N$_2$ | CO | CO$_2$ | H$_2$ | MeOH |
| U' | 550 | 80 | 63* | 34 | 0 | 1 | 0 | 0 | 0 | 0 |
| U" | 504 | — | 65 | 29 | 0 | 1 | 0 | 3 | 7 | 0 |
| V | 41 | 80 | 8 | 1 | 0 | 4 | 5 | 3 | 30 | 0 |
| W | 640 | — | 73 | 29 | 0 | 5 | 5 | 5 | 37 | 0 |
| X | 200 | 80 | 0 | 0 | 46 | 0 | 0 | 0 | 0 | 0 |
| Y | 1250 | — | 3 | 49 | 0 | 5 | 73 | 8 | 158 | 0 |
| Z | 40 | — | 3 | 0 | 0 | 5 | 73 | 8 | 158 | 0 |

| | Power requirements (kW) |
|---|---|
| Make-up gas compression | 109 |
| Circulator | 138 |
| Feedstock compression | 59 |
| Total | 306 |

*In addition to this amount of methane, there are also some higher hydrocarbons.

In Table 8 details are given of a process similar to that of Table 7 except that the auxiliary synthesis stage, i.e. reactor 34 and heat exchanger 32, is omitted.

TABLE 9

| | Temp °C. | Pres bara | Flow rate (kmol/h) | | | | | | | |
|---|---|---|---|---|---|---|---|---|---|---|
| | | | CH$_4$ | H$_2$O | O$_2$ | N$_2$ | CO | CO$_2$ | H$_2$ | MeOH |
| A | 20 | 30 | 94* | 0 | 0 | 2 | 0 | 0 | 0 | 0 |
| C | 500 | 30 | 31* | 102 | 0 | 1 | 0 | 0 | 0 | 0 |
| D | 830 | — | 10 | 68 | 0 | 1 | 14 | 10 | 80 | 0 |
| E | 40 | — | 10 | 0 | 0 | 1 | 14 | 10 | 80 | 0 |
| K | 66 | 73 | 10 | 0 | 0 | 1 | 8 | 9 | 66 | 1 |
| L | 40 | 73 | 241 | 1 | 0 | 109 | 90 | 73 | 745 | 9 |
| P | 240 | 80 | 246 | 1 | 0 | 112 | 171 | 89 | 953 | 9 |
| Q | 270 | 73 | 246 | 12 | 0 | 112 | 92 | 78 | 760 | 99 |
| R | 40 | — | 1 | 12 | 0 | 0 | 0 | 3 | 1 | 90 |
| T | 40 | — | 5 | 0 | 0 | 2 | 2 | 1 | 14 | 0 |
| U' | 550 | — | 63* | 34 | 0 | 1 | | 0 | | 0 |
| U" | 504 | — | 65 | 29 | 0 | 1 | 0 | 3 | 7 | 0 |
| V | 42 | 80 | 8 | 0 | 0 | 4 | 5 | 3 | 30 | 0 |
| W | 640 | — | 73 | 29 | 0 | 5 | 6 | 5 | 37 | 0 |
| X | 200 | 80 | 0 | 0 | 46 | 0 | 0 | 0 | 0 | 0 |
| Y | 1250 | — | 3 | 49 | 0 | 5 | 73 | 8 | 158 | 0 |
| Z | 40 | — | 3 | 0 | 0 | 5 | 73 | 8 | 158 | 0 |

| | Power requirements (kW) |
|---|---|
| Make-up gas compression | 112 |
| Circulator | 146 |
| Feedstock compression | 59 |
| Total | 317 |

*In addition to this amount of methane, there are also some higher hydrocarbons.

In this case the amount of methanol recovere in stream R was 90.3 kmol/h, i.e. a total yield similar to that of the Table 7 example. However the power requirement was greater, indicating that the use of the auxiliary synthesis stage in the Table 7 embodiment gives rise to a siguificant power saving.

In Table 9 below similar details are given for the first embodiment of FIG. 1, i.e. with the ex-loop gas being taken from the circulator recycle gas via line 66 and the reformed second stream being added via line 30 to the feed to the auxiliary synthesis stage.

TABLE 9

| | Temp °C. | Pres bara | Flow rate (kmol/h) | | | | | | | |
|---|---|---|---|---|---|---|---|---|---|---|
| | | | CH$_4$ | H$_2$O | O$_2$ | N$_2$ | CO | CO$_2$ | H$_2$ | MeOH |
| A | 20 | 30 | 94* | 0 | 0 | 2 | 0 | 0 | 0 | 0 |
| C | 500 | 30 | 31* | 102 | 0 | 1 | 0 | 0 | 0 | 0 |
| D | 830 | — | 10 | 68 | 0 | 1 | 14 | 10 | 80 | 0 |
| E | 40 | — | 10 | 0 | 0 | 1 | 14 | 10 | 80 | 0 |
| F | 60 | 50 | 10 | 0 | 0 | 1 | 14 | 10 | 80 | 0 |
| G | 260 | 47 | 11 | 1 | 0 | 8 | 52 | 18 | 172 | 35 |
| H | 40 | — | 0 | 1 | 0 | 0 | 0 | 1 | 0 | 32 |
| K | 60 | 73 | 11 | 0 | 0 | 8 | 52 | 17 | 172 | 3 |
| L | 40 | 73 | 145 | 1 | 0 | 101 | 52 | 52 | 562 | 6 |
| P | 240 | 80 | 156 | 735 | 0 | 109 | 104 | 169 | 735 | 8 |
| Q | 270 | 73 | 156 | 12 | 0 | 109 | 56 | 58 | 605 | 67 |

TABLE 9-continued

| | Temp °C. | Pres bara | Flow rate (kmol/h) | | | | | | | |
|---|---|---|---|---|---|---|---|---|---|---|
| | | | CH$_4$ | H$_2$O | O$_2$ | N$_2$ | CO | CO$_2$ | H$_2$ | MeOH |
| R | 40 | — | 0 | 11 | 0 | 0 | 0 | 2 | 1 | 61 |
| T | 40 | — | 3 | 0 | 0 | 2 | 1 | 1 | 12 | 0 |
| U' | 550 | 50 | 63* | 34 | 0 | 1 | 0 | 0 | 0 | 0 |
| U" | 495 | — | 65 | 29 | 0 | 1 | 0 | 3 | 7 | 0 |
| V | 40 | 5 | 8 | 0 | 0 | 6 | 3 | 3 | 31 | 0 |
| W | 640 | — | 73 | 29 | 0 | 7 | 3 | 6 | 38 | 0 |
| X | 200 | 80 | 0 | 0 | 47 | 0 | 0 | 0 | 0 | 0 |
| Y | 1250 | — | 1 | 49 | 0 | 7 | 73 | 7 | 162 | 0 |
| Z | 40 | — | 1 | 0 | 0 | 7 | 73 | 7 | 162 | 0 |

| | Power requirements (kW) |
|---|---|
| Make-up gas compression | 199 |
| Circulator | 105 |
| Feedstock compression | 30 |
| Total | 334 |

*In addition to this amount of methane, there are also some higher hydrocarbons.

The amount of methanol recovered via lines H and R is 93.5 kmol/h. Thus there is a 3% increase in output compared to the embodiment shown in Table 7, at the expense of an increase in the power requirement of about 28 KW. On the other hand, the oxygen has to be supplied only at 50 bar abs., as opposed to 80 bar abs., and so this will give a power saving. A particular advantage of the Table 9 embodiment is the decreased amount of gas circulating in the loop and the decrease in the circulation power required. This would enable the output of an existing plant to be increased significantly by the addition of the auxiliary synthesis stage.

I claim:

1. A process for the production of a hydrogen-containing synthesis gas from a desulphurised hydrocarbon feedstock comprising a) subjecting a first stream of said desulphurised feedstock to primary catalytic steam reforming, and then cooling of the resultant reformed first stream; b) subjecting a second stream of said desulphurised feedstock to a pre-reforming step of adiabatic low temperature steam reforming, followed by partial oxidation of the resultant pre-reformed second stream using an oxygen-containing gas, to form a reformed second stream, cooling the reformed second stream; and c) mixing the cooled reformed first and second streams.

2. A process according to claim 1 wherein the cooled reformed first and second streams are fed as make-up gas to a methanol synthesis loop having a catalytic methanol synthesis stage and a separation stage with recycle of unreacted gas from the separation stage to the synthesis stage, and methanol is synthesised in said synthesis stage from a mixture of the make-up gas and recycle gas.

3. A process according to claim 2 wherein a hydrogen-containing gas taken from the loop is added to the pre-reformed second stream before subjecting the latter to partial oxidation.

4. A process according to claim 3 wherein, prior to the partial oxidation stage, the second feedstock stream is compressed, the partial oxidation of the second feedstock stream is effected at a pressure greater than that at which the primary reforming of the first stream is effected, and the primary reformed first stream is compressed prior to mixing with the cooled reformed second stream.

5. A process according to claim 3 comprising a step of synthesising methanol from the reformed first or second streams, or from a mixture of the reformed first and second streams, in an auxiliary synthesis stage, at a pressure above that employed for the primary reforming of the first stream and below the pressure at which methanol is synthesised in the synthesis loop, before the relevant stream is added to the synthesis loop.

6. A process according to claim 5 wherein synthesised methanol is separated from the product from the auxiliary methanol synthesis stage, and the unreacted gas from that separation is further compressed before addition to the synthesis loop.

7. A process according to claim 3 wherein the synthesis loop includes a step of compression of the unreacted gas from the loop separator to the synthesis pressure, and the stream of hydrogen-containing gas is taken from the loop at said synthesis pressure.

8. A process according to claim 7 wherein the reformed second stream, without further compression, is added to the loop at the loop compression stage inlet pressure.

9. A process according to claim 3 wherein the partial oxidation stage is non-catalytic and the pre-reforming stage is omitted.

10. A process for the production of methanol in a synthesis loop wherein methanol is synthesised from synthesis gas formed from a mixture of make-up gas and recycle gas at an elevated synthesis pressure, and synthesised methanol is separated to give a stream of unreacted gas, part of which is recycled as said recycle gas, said make-up gas being obtained by steam reforming a desulphurised hydrocarbon feedstock at an elevated reforming pressure that is below said synthesis pressure followed by cooling, water removal and compression to said synthesis pressure, and is characterised in that a stream of gas is taken from said methanol synthesis loop from a point between, in flow direction, the step of separation of the synthesised methanol and the step of methanol synthesis, and this stream taken from the loop is mixed with a further quantity of desulphurised hydrocarbon feedstock at a pressure above said reforming pressure, the resulting mixture is reacted adiabatically with a stream of oxygen to give a hot gas stream which is then cooled and returned to the synthesis loop.

* * * * *